(12) United States Patent
Chadwick et al.

(10) Patent No.: US 11,526,541 B1
(45) Date of Patent: Dec. 13, 2022

(54) METHOD FOR COLLABORATIVE KNOWLEDGE BASE DEVELOPMENT

(71) Applicant: Live Circle Inc., Ridgewood, NJ (US)

(72) Inventors: Charles Chadwick, Ridgewood, NJ (US); Samuel Brotherton, Park City, UT (US)

(73) Assignee: Live Circle, Inc., Ridgewood, NJ (US)

( * ) Notice: Subject to any disclaimer, the term of this patent is extended or adjusted under 35 U.S.C. 154(b) by 140 days.

(21) Appl. No.: 17/074,567

(22) Filed: Oct. 19, 2020

Related U.S. Application Data

(60) Provisional application No. 62/916,793, filed on Oct. 17, 2019.

(51) Int. Cl.
*G06F 17/00* (2019.01)
*G06F 16/332* (2019.01)
*G06F 40/30* (2020.01)
*G06F 16/36* (2019.01)
*G06N 5/02* (2006.01)

(52) U.S. Cl.
CPC .......... *G06F 16/3329* (2019.01); *G06F 16/36* (2019.01); *G06F 40/30* (2020.01); *G06N 5/022* (2013.01)

(58) Field of Classification Search
None
See application file for complete search history.

(56) References Cited

U.S. PATENT DOCUMENTS

| | | | |
|---|---|---|---|
| 7,742,911 B2* | 6/2010 | Chotimongkol | G10L 15/1822 704/4 |
| 9,367,608 B1* | 6/2016 | Zhang | G06F 16/3331 |
| 2017/0337180 A1* | 11/2017 | Wang | G06F 40/253 |
| 2019/0155907 A1* | 5/2019 | Park | G06F 40/56 |
| 2019/0311003 A1* | 10/2019 | Tonkin | G06N 5/022 |

* cited by examiner

*Primary Examiner* — Satwant K Singh
(74) *Attorney, Agent, or Firm* — DeLucia, Mlynar & Associates LLP

(57) ABSTRACT

A knowledge base is collaboratively developed by receiving language input from at least one editor, featurizing it into language elements, extracting predicate sets that are missing predicate arguments, querying editors for input regarding the missing arguments, and updating the knowledge base with suitable predicate arguments and other language elements provided by the editors.

15 Claims, 5 Drawing Sheets

METHOD FOR COLLABORATIVE KNOWLEDGE BASE DEVELOPMENT

CROSS-REFERENCE TO RELATED APPLICATIONS

This application claims priority to and the benefit of U.S. provisional application Ser. No. 62/916,793 filed on Oct. 17, 2019 and entitled Artificial Intelligence System and Method for Use, which is commonly assigned and the contents of which are expressly incorporated herein by reference. This application is related to the copending U.S. patent application Ser. No. 17/074,617, by Charles Chadwick and Samuel Brotherton entitled Automated Predictive Care System filed on Oct. 19, 2020, the contents of which are expressly incorporated herein by reference, and is also related to the copending U.S. patent application Ser. No. 17/074,270, by Charles Chadwick and Samuel Brotherton entitled Voice Analyzer For Interactive Care System filed on Oct. 19, 2020, the contents of which are expressly incorporated herein by reference.

STATEMENT REGARDING PRIOR DISCLOSURES BY THE INVENTOR OR A JOINT INVENTOR

Chadwick, Charles, "Live Circle Family Caregiver Conversations", (Confidential PowerPoint presentation), 22 Feb. 2019. Comcast Center, 1701 John F Kennedy Blvd., Philadelphia, Pa. 19103.

Demiris, George et. al, "Spoken words as biomarkers: using machine learning to gain insight into communication as a predictor of anxiety", Journal of the American Medical Informatics Association, 27(6), 6 May 2020, 929-933.

FIELD OF THE INVENTION

The present invention relates to knowledge base development methods and systems.

BACKGROUND

In the past, known artificial intelligence computational tools involving probabilistic programming have been used to create digital knowledge bases based on language analysis. Such knowledge bases are a collection of data representing entities, facts, and relationships that conform to a predefined data model. Such knowledge bases help machines to understand humans, language, and the world. See Wang, Daisy Zhe, "A Probabilistic Knowledge Base System", (PowerPoint presentation). Data Science Research CISE University of Florida, 2013, the contents of which are incorporated herein by reference in their entirety.

SUMMARY OF THE INVENTION

According to an aspect of the invention, an automated method for collaboratively developing a knowledge base with information from a plurality of editors includes the steps of receiving, from at least one editor, a language input; featurizing the language input to produce featurized data; extracting, based upon the featurized data, an incomplete predicate set comprising a predicate head; determining whether a predicate argument is present in the incomplete predicate set; and querying at least one of the plurality of editors for an input regarding the predicate argument.

According to another aspect of the invention, an automated method for collaboratively developing a knowledge base with information from a plurality of editors includes the steps of designating a plurality of editors; providing to at least one of the plurality of editors a knowledge base activity information comprising an unfulfilled predicate argument information associated with an unfulfilled predicate argument; inviting editor input from at least one of the plurality of editors regarding the unfulfilled predicate argument information; fulfilling the unfulfilled predicate argument information based upon the editor input to generate a complete predicate set; and storing the complete predicate set in the knowledge base.

BRIEF DESCRIPTION OF DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
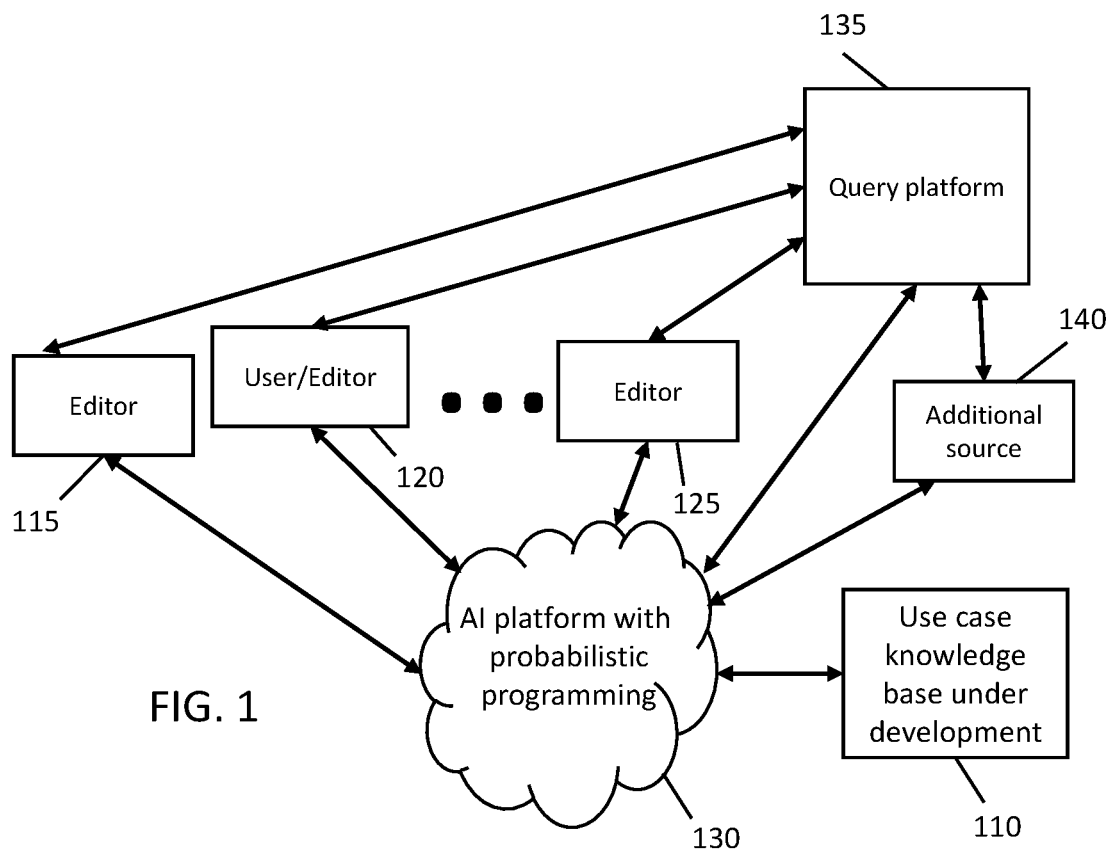
FIG. 1 is a block diagram illustrating collaborative development of a use case knowledge base in accordance with various embodiments of the present invention.

So that the manner in which the features and advantages of embodiments of methods and systems of the present invention may be understood in more detail, a more particular description of the present invention briefly summarized above may be had by reference to certain embodiments thereof that are illustrated in the appended drawings, which form a part of this specification. The drawings illustrate only certain embodiments of the present invention and are, therefore, not to be considered limiting of the scope of the present invention which includes other useful and effective embodiments as well. For ease of description and understanding, the following embodiments are discussed mainly in connection with industrial system control applications but can be advantageously implemented in medical applications, financial systems, other algorithmically optimized control systems, and the like.

Machine-learning based expert systems that assist users in accomplishing goals may rely on probabilistic knowledge bases. Probabilistic knowledge bases can comprise language and language-based elements. Artificial Intelligence (AI) computational tools using probabilistic programming analyze, update, and manage probabilistic databases comprised of language and language-based elements to accomplish a variety of applications. Examples include the preferred methods disclosed in the co-pending applications identified above and incorporated herein by reference.

The probabilistic knowledge bases can include a number of specific elements of language, spoken and written. These include, for spoken language, qualities of the associated audio signal such as loudness, loudness range, power, peak-to-average power ratio, and pitch characteristics including centroid, crest, flatness, kurtosis, roll-off, skewness, slope and spread. For written language, and text generated from voice-to-text conversion, a large number of language elements are available to analyze. They include individual words, referred to as tokens, combinations of words that ordinarily go together referred to as ngrams (e.g., "heart attack," n being 2 in this example), and word "vectors," which represent a token or ngram together with its potential substitutes, such as synonyms.

When analysis is performed on spoken and written language to identify the foregoing language elements, the elements may be referred to as "features," and the automated development of language features may be referred to as "featurization."

In addition, there are ways to arrange words obtained from language analysis that facilitate the operation of the AI computational tools. Specifically, tokens, ngrams and vectors can be used to determine subject-object-verb sets that can be used by the AI tools to develop the characterizations.

The AI computational tools examine the language elements to recognize and extract facts, things that can be known about a thing, as "probabilistic predicates." A "predicate" (also known as a "label") comprises a predicate head and a predicate argument (also known as the "predicate body"). For example, if the thing is a banana, a characteristic that can be known about it is its color. And that color, in the case of a banana, is yellow. For an individual, one thing that can be known is age, for example, 55 years. For the purposes of AI computational tools, a statement of the topic of interest, for example color or age, is referred to as the "predicate head." And the answer, yellow or 55, respectively, is referred to as the "predicate argument." Note that the arguments are susceptible to change and to being updated over time. Yellow at a later date might be brown. Age at a later date will be 56 years.

A predicate head together with one or more associated arguments may be referred to as a predicate set.

In certain applications, it is useful to develop a detailed language-based knowledge base that represents a particular scenario or set of circumstances that an individual might find themselves in. These scenarios or sets of circumstances may be referred to as "use cases." Such a knowledge base can be used by AI computational tools using probabilistic programming to guide a user through the use case. An example use case is a son or daughter managing support for an elderly parent who has just undergone heart surgery, while at the same working through the insurance coverage process, and also maintaining an appropriate life balance with immediate family at home. Another use case may be the circumstance of endeavoring to improve one's golf game.

It will be understood that the more detailed and accurate the use case knowledge base is for representing a given use case, the more effective the expert system can be at guiding a user through the use case. A preferred knowledge base includes as much relevant information as possible regarding what circumstances can arise, and what body of things, information and relationships are relevant to the use case.

For example, if a use case is, "improving an individual's golf game," it is desirable for the use case knowledge base to include predicate sets for every type of golf club and other equipment involved in golf. In addition, the use case should include predicate sets reflecting every golf course throughout the world, the names and qualities of golf all coaches, the names of golforiented magazines and television programming, how weather conditions can effect a golf game, different types of golf games such as team play, all golf tournaments and their locations and prizes, and the like. Of course, perfect knowledge may be impossible or impractical to obtain.

A knowledge base benefits not only from the broadest universe of relevant predicates, but also from as many examples as possible of language input that indicates a particular predicate and fulfills the predicate's argument. For example, if a predicate set comprises header "where is the pain" and argument "bodypart", then the system will benefit from having processed hundreds of examples of language input that indicate and fulfill the missing argument (bodypart) of the predicate set. Such as, "My leg hurts", or "I'm having a sharp pain in my chest", or "Ouch!". The final example, "Ouch!" is notable because that language input indicates the predicate set, but doesn't fulfill the argument, "bodypart". As will be described more fully, sources of that input can be queried by the system to fulfill the argument.

The more detailed and all-encompassing the use case knowledge base is, including large numbers of examples of language input that indicates a particular predicate and fulfills the predicate's argument, the better the system will be at understanding the meaning and relevance of communications from and relating to users, guiding users towards goals, and communicating with users.

Preferred embodiments of the present invention build a use case knowledge base collaboratively by facilitating input from multiple authorized editors, and in some embodiments by the users of the system themselves. The editors and users interact with the system with natural language, that language is processed and a robust use case knowledge base is built, and, once approved by editors, implemented as a live use case on the preferred platform for the use case.

As the use case knowledge base is being developed the editors may each have visibility to the use case knowledge base elements derived not only from their own input, but also that derived from other's input. The editors may be designated with different authority levels determining their permission to influence, change and modify the input from others. In this fashion, a plurality of editors collaboratively contribute to, and refine, the use case knowledge base.

Collaboratively developing a knowledge base according to a preferred embodiment of the inventive method involves deriving language features from language input. One or more editors are identified to interact with the system. The editors may include users of the system. Users are individuals who are not only engaged with the system to develop the use case knowledge base, but in addition are receiving guidance from the system to traverse a use case that is the subject of the knowledge base.

FIG. 1 is a block diagram providing a overview of an automated method for collaboratively developing a knowledge base with information from a plurality of editors, according to a preferred embodiment of the present invention. The functionality illustrated in FIG. 1 is describe in further detail in connection with FIGS. 2, 3 and 4.

As shown in FIG. 1, use case knowledge base under development 110 is developed based on input from, and interaction with, editors 115, 120 and 125. In certain preferred embodiments editors may also be users of the system, for example user/editor 120 as shown. There may be any number of editors for any specific embodiment.

An AI platform with probabilistic programming 130 designates and authorizes which individuals may interact with the system in an editor capacity. AI platform 130 may also assign editors authority levels that determine the extent to which that editor may to influence, change and modify the input effecting the development of use case knowledge base under development 110.

Editors 115, 120, and 125 provide language input to AI platform 130. The language input is preferably concerning topics that are relevant to the use case of use case knowledge base under development 110. AI platform 130 analyzes the language input. AI platform 130 determines whether it will be useful to solicit follow up input from any particular editor concerning information that has been provided.

If AI platform 130 determines that additional information is useful, AI platform 130 may solicit such information in a variety of ways. AI platform 130 may query an editor directly by communications modalities including, as examples, text, email and text-to-speech. Alternatively, AI platform 130 may alternatively post queries to a query platform 135 that is accessible to editors who have been provided sufficient authority by AI platform 130 to access and interact with query platform 135. In preferred embodiments, query platform 135 may be an electronic bulletin board accessible over the internet.

Additionally, if AI platform 130 determines that additional information is useful, AI platform 130 may solicit information from additional source 140. Additional source 140 may be, for example, an external database expected to hold information relevant to the use case of use case knowledge base under development 110. Alternatively, additional source 140 may be a third-party expert in a particular relevant field. Additional source 140 may communicate directly with AI platform 130 and may be provided access to query platform 135.

Figure 2B:
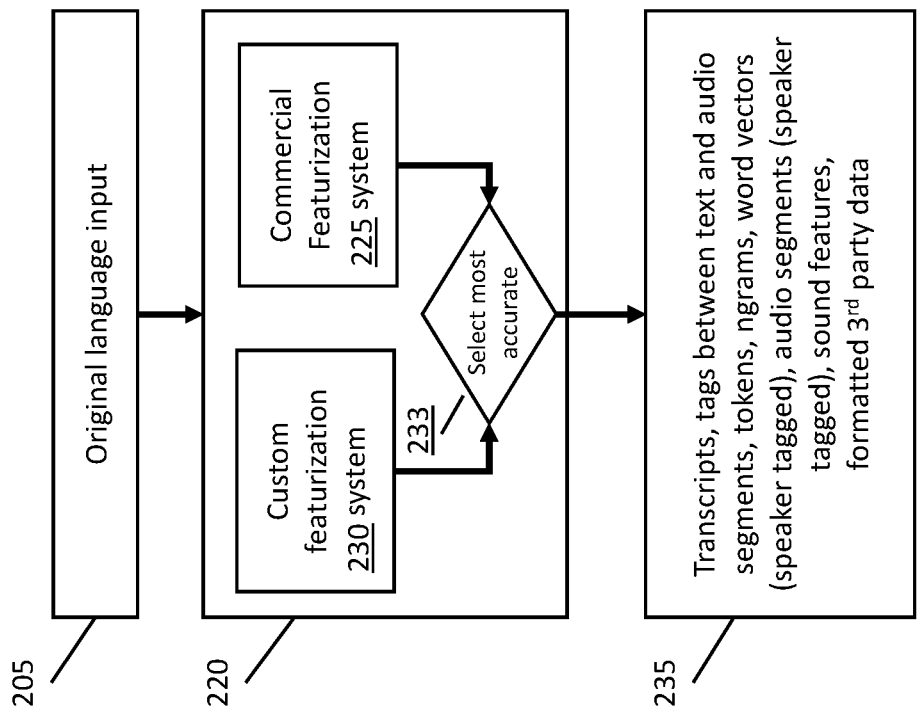
FIG. 2B is a flow diagram illustrating steps of an automated method for featurizing language input in accordance with various embodiments of the present invention.
Figure 2A:
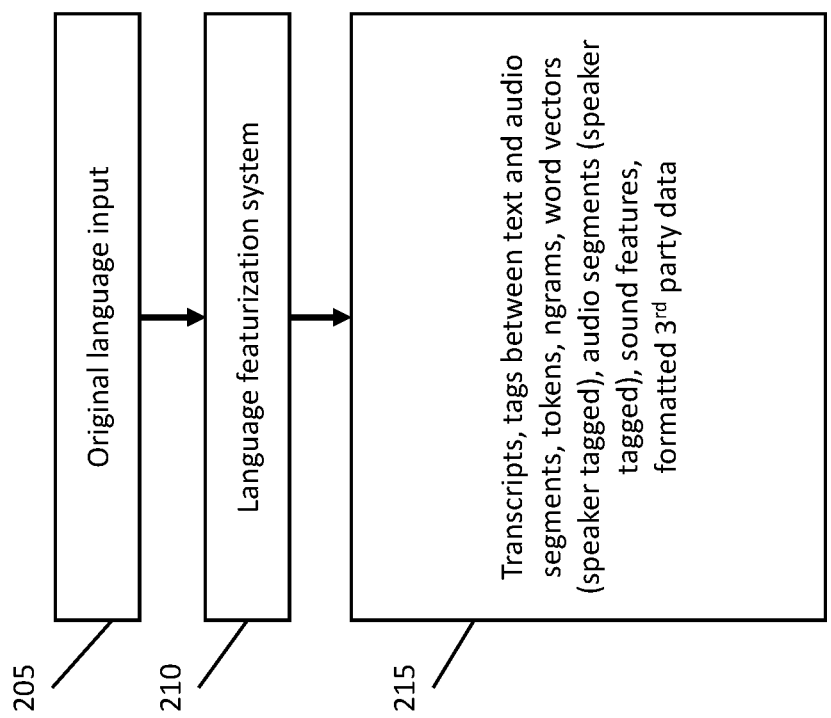
FIG. 2A is a flow diagram illustrating steps of an automated method for featurizing language input in accordance with various embodiments of the present invention.

Turning now to the remaining figures for further detail regarding a preferred embodiment of the present invention, FIGS. 2A and 2B are flowcharts illustrating how, according to a preferred embodiment, language input by the editor(s) is featurized into language elements that can be operated on by AI computational tools using probabilistic programming. In certain preferred embodiments, the probabilistic programming language and platform ProbLog is used.

The use case knowledge base according to the preferred embodiment is a probabilistic knowledge base. Language, spoken and written, can be analyzed, and broken down into elements permitting artificial intelligence (AI) computational tools employing probabilistic programming, and novel improvements to those tools, to predict the likely status and situational context of individuals and things. The probabilistic programming generates probabilities that a given fact is true and can generate new facts from inference using extracted facts, rather than follow strict axioms or rules of traditional expert systems that rely on only true or false logical conditions. Instead, the inventive system relies on neural networks trained on data and logical relationships between facts to assign a weight to initial facts, including those associated with initial user status and situational context. And, through the course of operations, the system uses new facts, extracted from user input or input about the user to update the probabilities.

In the preferred embodiment, a probabilistic programming language, such as Problog, may be chosen. In Problog, the representation 1.0::is_named(User123, "Tom Garvin") could be read as "We are 100% sure that User123's name is Tom Garvin", and 0.7::took_medication_on_day(User123, "statin", Mar. 10, 2018) could be read as "We are 70% sure that Tom Garvin took his statins on Mar. 10, 2018.

The use of probability does not preclude certainty, as per above that User123 is "Tom Garvin". However, it recognizes that in real world that facts "change." While it may be true that a weekly work schedule exists, it may also be that half the time a weekly work schedule changes and that on some days it is more likely to change than on others. These facts enter the system through extractions and are considered "facts", even if only probabilities. Probabilities likewise exist for a person's state of mind. The invented system can determine the likelihood of a certain state of mind or health using neural networks trained on studied states of mind and data used to train the neural network on these states. Similarly, for an entity such as a pharmacy, its hours of service and medications in stock can be determined and characterized on the basis of probability.

Referring to FIG. 2A, original language input is received at step 205. As an example, this may be the audio associated with a phone conversation between the cared-for user, and another user, for example a nurse. At step 210 language input is received by a language featurization system that comprises automated speech recognition functionality, text based natural language processing functionality, and audio signal processing functionality. The language featurization system may comprise only readily available language and audio processing elements, as will be appreciated by one skilled in the art. Alternatively, according to a preferred embodiment, the language featurization system may be a novel customized system as will be more fully described in connection with FIG. 2B.

At step 215, the language featurization system featurizes the received language input, generating language features. These features include i) a text transcript, ii) audio broken down into audio segments which may represent individual utterances, sentence or sentence fragments, the segments tagged to identify the speaker, iii) tokens which represent individual words, iv) ngrams which represent word combinations that when taken together have a common meaning apart from what the words would mean individually, v) word vectors associated with the tokens and ngrams, which represent a token or ngram together with its potential substitutes such as synonyms, the vectors tagged to identify the speaker vi) sound features such as loudness, loudness range, power, peak-to-average power ration, pitch characteristics including centroid, crest, flatness, kurtosis, roll-off, skewness, slope and spread, and vi) formatted third party data such as named entities including persons, places and brands. The featurized data is stored electronically so as to be accessible to the rest of the system during the execution of the method.

In comparison, FIG. 2B illustrates an alternative embodiment of step 220 that involves at least two language featurization systems, language featurization system 225 and language featurization system 230. In this representative embodiment, system 225 may comprise commercially available automated speech recognition functionality, text based natural language processing functionality, and audio signal processing functionality.

In addition, this version of the inventive method includes custom trained language featurization system 230. Specifically, as will be more fully described, language featurization system 230 is trained using audio content taken from a large collection of conversations that i) are similar in nature to common use cases, involving for example older subjects and medically related use cases, and ii) occur during a clinical trial intervention before which and after which subjects in the clinical trial are tested using clinically validated health assessments (e.g. GAD). This audio content can be referred to as reference audio content or reference speech data. The classifier subsystem and classifier functionality that generates scores associated with health assessment may be trained on the same reference speech data. Recall that reduced anxiety and other mental health measures such as improved quality of life comfort level are often stated or inferred goals of a cared-for user or user. Therefore, preferred embodiments of the inventive method include the capability of determining these levels for the users. Moreover, training based on the particularly pertinent reference speech data allows the custom language featurization system to more reliably "understand," and therefore better featurize language input, as compared to a language featurization system comprising only commercially automated speech recognition functionality, text based natural language processing functionality, and audio signal processing functionality.

At step 233, the running outputs of language featurization system 225 and 230 are measured by the language featurization system functionality for confidence level with respect to calculated features and text transcription, and the featurization data found most accurate is included in the featurized output at step 235.

Figure 3:
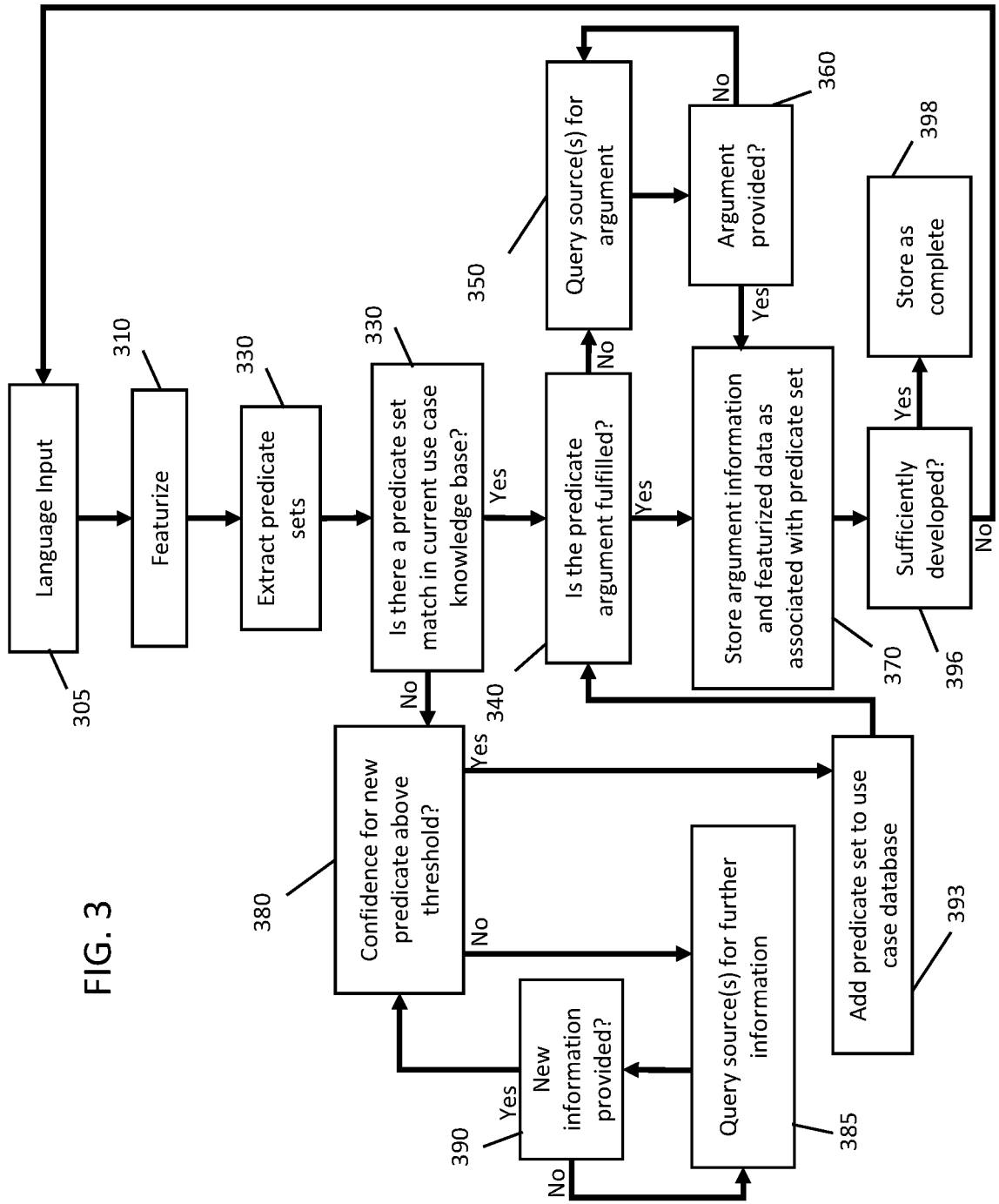
FIG. 3 is a flow diagram illustrating steps of an automated method for developing a knowledge base from language input in accordance with various embodiments of the present invention.

FIG. 3 is a block diagram illustrating how a preferred embodiment of the present invention builds the use case knowledge base from language input from one of the collaborating editors. At step 305, the editor provides language input to the system. In preferred embodiments, this may be by way of voice communication, text input or video input. In preferred embodiments the subject of the language input is intended to be relevant to the use case for the knowledge base under development. The editor to talks about the subject matter of the use case, or, alternatively types the subject matter into a web interface used for the collaboration. This will provide more fruitful input for building the use case knowledge base.

At step 310, the language input is featurized. In the preferred embodiment, it is featurized according to the functionality illustrated in FIG. 3B. At step 330, AI computational tools based on probabilistic programming derive predicate sets from the language input based on the featurized data. Deriving predicate sets from such featurized data is referred to as "extracting" predicate sets.

At step 330, it is determined whether the extracted predicate set is already present in the use case knowledge base under development. If the predicate set is present, then at step 340 the extracted predicate set is analyzed to determine whether it includes a predicate argument.

Referring to an example offered above, the word "Ouch!" input by an editor may be recognized by the AI that analyzes the associated featurized data to indicate the predicate set, header "where is the pain" and argument "bodypart." It may be determined at step 330 that the corresponding predicate set is already present in the use case knowledge base under development. However, at step 340 it is determined that no predicate argument is present in the langue input. "Ouch!" identifies the predicate set, but information that can fulfill the argument, "bodypart," has not been provided.

Under the foregoing circumstances, at step 350 the editor is queried, and potentially others, to supply the information required to fulfill the argument. The query may be presented, as an example, by the preferred method of posing a natural language question to the editor, such as, "It seems you're experiencing some pain. What hurts?" Such queries may be posted on line in social or other media or on a bulletin board used by the editors, a portion of which may be made public, beyond the editors, in order to solicit answers, which when received, may be curated by the editors based on rules set for the collaboration by the controller. Alternatively, as another example, an appropriate query may be posted to a bulletin board accessed by all editors. The question may be, "Please respond telling us what body-part you assume might be in pain when someone exclaims "Ouch!"" "As an example the majority of responders might respond "toe." At step 360, it is determined that "toe" has been provided and is an appropriate argument for this predicate set that should be added to the knowledge base. More generally, at step 360 it is determined whether argument information has been provided. If argument information has not been provided, then the editor and others may be queried again at step 350, repetitively a predetermined number of times. At step 370, if argument information has been provided, then it is stored in the knowledge base as an argument to the predicate set, along with associated featurized information.

Returning to step 330, if no match to the extracted predicate in the use case knowledge base under development is found, then at step 380 a confidence determination is made based on probabilistic programing results and a predetermined threshold, If the confidence level is sufficiently high, the extracted predicate is added to the use case knowledge base. If the threshold is not met, at step 385 the editor and potentially other sources are queried for further information which may add to the reliability of the extracted predicate. As an example, the possible predicate set header "fall risk" and argument "where" may be extracted from language input "When I showered it was slippery." In the example, at step 380 it may be determined based on probabilistic programing that the preliminary determination of that predicate set is not reliable enough. In the example, at step 385 the method may query to the bulletin board or the editor, "What happens when it is slippery in the shower?," and "What places tend to be slippery?"

If at step 390 it is determined that information has not been provided, then the bulletin board may be queried again at step 385, repetitively a predetermined number of times. If at step 390 it is determined that information has been provided, then at step 380 the confidence level is determined again, having the benefit of the information that was provided at step 390.

If the confidence threshold is met at step 380, then at step 393 the newly extracted predicate set is added to the use case knowledge base. At step 340 it is determined whether the language input associated with the newly added predicate set includes argument information. If it does not, queries may be made as described above. If argument information is present, then at step 370 it is stored in the knowledge base as an argument to the predicate set, along with associated featurized information.

Figure 4:
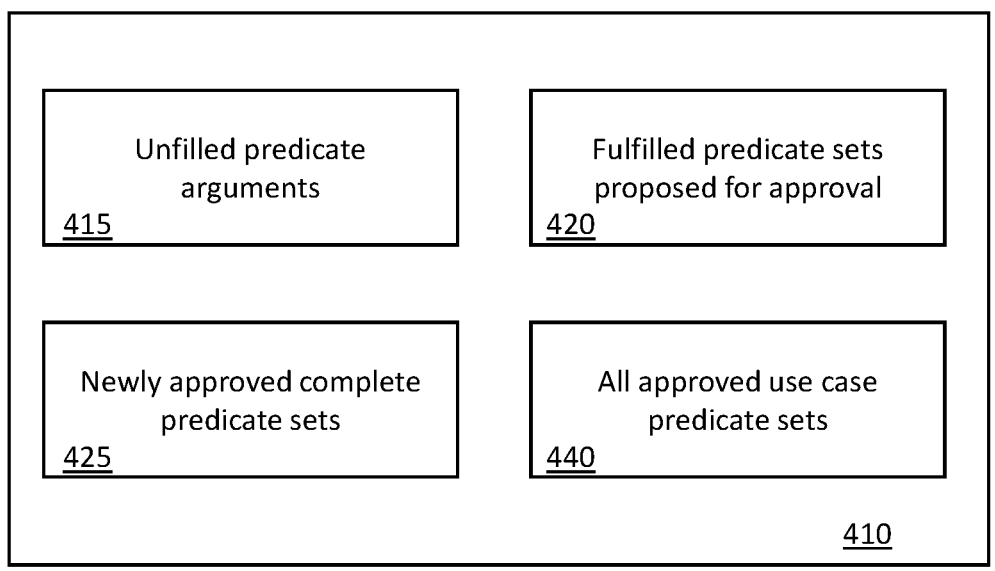
FIG. 4 is a block diagram illustrating use case knowledge base development activity information in accordance with various embodiments of the present invention.

FIG. 4 is a block diagram illustrating information provided to editors in the preferred embodiment relating to the ongoing development of the use case knowledge base. As will be more fully discussed, the information may be made available to the editors in a variety of ways. Editors may be assigned differing levels of authority for providing responsive input, and for influencing, changing, or modifying the information.

Specifically, use case knowledge base activity information 410 comprises unfulfilled predicate argument information 415. Unfulfilled predicate argument information 415 may be a list of unfulfilled arguments, for which editors may offer input. Alternatively, unfulfilled predicate argument information 415 may be natural language questions soliciting input that will be helpful for fulfilling the argument.

Use case knowledge base activity information 410 further comprises fulfilled predicate sets proposed for approval information 420. Fulfilled predicate sets proposed for approval information 420 relates to predicates that have been recently extracted from language input but not yet added to the use case knowledge base. In the preferred embodiment, fulfilled predicate sets proposed for approval information 420 invite the editors to review the proposed predicate sets and to offer their view regarding whether the predicate sets should be added to the use case knowledge base.

In the preferred embodiment, use case knowledge base activity information 410 further comprises newly approved complete predicate sets 425. This gives editors visibility to the evolving state of the use case knowledgebase. Similarly, use case knowledge base activity information 410 further comprises all approved use case predicate sets information 440. This is a list of all predicate sets currently found in the use case knowledge base. This information is helpful to give editors and appreciation for the level of completeness of a use case knowledgebase under development.

Use case knowledge base activity information 410 may be made available to editors in a variety of ways. As an example, in a preferred embodiment use case knowledge base activity information 410 may be provided, all or in part, to an electronic bulletin board accessible to editors based on the editor's level of authority. Alternatively, use case knowledge base activity information 410 may be displayed to a user on their computer or mobile device as they interact with the system. As another example, use case knowledge base activity information 410 may be presented in a report to editors delivered by email. Ongoing access to, and interaction with, use case knowledge base activity information 410, together with multiple editors providing language input ostensibly relevant to the use case, results in rapid development of a very robust use case knowledge base.

Figure 5:
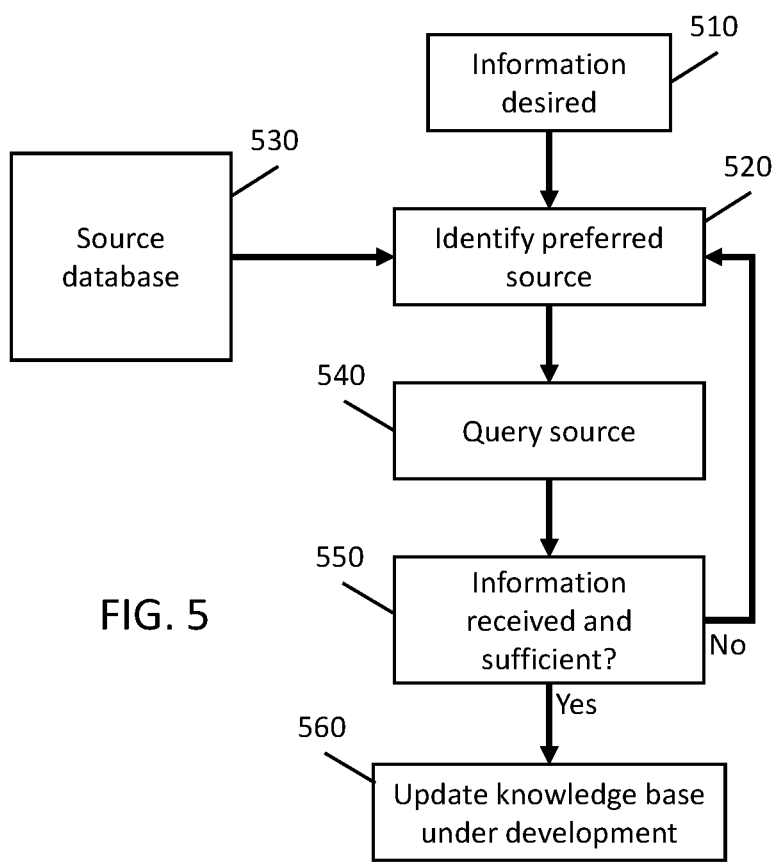
FIG. 5 is a flow diagram illustrating steps of an automated method for intelligently determining preferred sources for input in accordance with various embodiments of the present invention.

As has been described, follow-up information concerning, for example proposed predicate sets and unfulfilled predicate arguments may be desired. As illustrated in FIG. 5, a preferred embodiment of the present invention provides for improved quality of follow-up information solicited, by being selective about which sources are queried for the information. Specifically, at step 510 it is determined that follow-up information is desired. At step 520, a preferred source of that information is selected. That source is selected based upon source reference database provided at step 530.

In a preferred embodiment, source reference database 530 includes a list of sources available, for example each authorized editor, and significantly, detailed characteristics about each source. The characteristics may include, as examples, specific skill set and area of expertise, schedule and availability, history of providing helpful information in connection with prior queries, cost of input if application, personal traits such as age and gender, areas of personal interest and hobbies. It will be recognized that more and different source characteristic information may be included.

At step 540, the selected source is queried by any one of the communications modalities already described, or others. At step 550, it is determined whether information has been received in response to the query, and whether it is sufficient to address the issue that prompted the query. If sufficient information was received, then at step 560 the use case knowledge base under development is updated accordingly. If no information has been received, or the information is determined to be insufficient, has not been provided, then further queries may be initiated for a predetermined number of cycles. Specifically, another or the same preferred source is identified at step 520, and the steps repeat.

Some portions of this description describe the embodiments of the invention in terms of algorithms. These operations, while described functionally, computationally, or logically, are understood to be implemented by computer programs or equivalent electrical circuits, micro-code, or the like. The described operations may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to herein may include a single processor or may be implemented with architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

The various embodiments can be further implemented in a wide variety of operating environments, which in some cases can include one or more user computers or computing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially available operating systems and other known applications for purposes such as database management. These devices can also include other electronic devices, such as dummy terminals, virtual terminals, thin-clients, and other devices capable of communicating via a network.

Embodiments can utilize at least one network that would be familiar to those skilled in the art for supporting communications using any of a variety of commercially available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network, or any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python, or TCL, as well as combinations thereof. The server(s) may also include database servers, including without limitation those commercially available from Oracle®, Microsoft®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element, or keypad) and at least one output device (e.g., a display screen, a display device, printer, or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed, and/or removable storage devices as well as storage media for temporarily and/or more permanently containing, storing, transmitting, and retrieving computer-readable information. The system and various devices also can include a number of software applications, modules, services, or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets, APIs, scripts, and the like), or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments and that many modifications and variations are possible.

The foregoing description of the embodiments of the invention has been presented for the purpose of illustration; it is not intended to be exhaustive or to limit the invention to the precise forms disclosed. The description and drawings are, accordingly, to be regarded in an illustrative rather than a restrictive sense. The language used in the specification has been principally selected for readability and instructional purposes. It is therefore intended that the scope of the invention be limited not by this detailed description and drawings, but rather by any claims that issue based on this application. It will, however, be evident that various modifications and changes may be made thereunto without departing from the broader spirit and scope of the invention as set forth in the claims.

What is claimed is:

1. An automated method for collaboratively developing a knowledge base with information from a plurality of editors comprising the steps of:
   receiving, from at least one editor, a language input;
   featurizing said language input to produce a featurized data;
   extracting, based upon said featurized data, an incomplete predicate set comprising a predicate head;
   determining whether a predicate argument is present in said incomplete predicate set; and
   querying at least one of the plurality of editors for an input regarding said predicate argument.

2. The method of claim 1, wherein the step of querying comprises the step of communicating to the at least one of the plurality of editors a natural language question regarding said predicate argument.

3. The method of claim 1,
   wherein the step of querying comprises the step of posting a query to an electronic bulletin board; and
   further comprising the step of requesting the at least one of the plurality of editors to provide input regarding said predicate argument.

4. The method of claim 1, further comprising the steps of:
   receiving an input predicate argument from at least one of the plurality of editors;
   pairing said input predicate argument with said predicate head to generate a complete predicate set; and
   storing said complete predicate set in said knowledge base.

5. The method of claim 1, further comprising the steps of:
   receiving an input predicate argument from at least one of the plurality of editors; and
   storing said featurized data and said input predicate argument as a plurality of exemplary language features associated with said incomplete predicate set.

6. The method of claim 1, wherein the step of determining comprises the step of determining whether a complete version of said incomplete predicate set is already present in a use case knowledge base; and retrieving said complete version from said use case knowledge base.

7. The method of claim 1, wherein the plurality of editors each have a designated authority level determining a permission level for providing said input regarding said predicate argument.

8. The method of claim 1, further comprising the steps of:
receiving an input predicate argument from at least one of the plurality of editors;
determining if a predicate set confidence level is above a threshold;
pairing said input predicate argument with said predicate head to generate a complete predicate set; and
storing said complete predicate set in said knowledge base.

9. The method of claim 1, further comprising the steps of:
receiving an input predicate argument from at least one of the plurality of editors;
determining if a predicate set confidence level is above a threshold;
determining whether a predicate argument information has been provided in said featurized data; and
storing said predicate argument information and said featurized data as exemplary language features associated with a complete predicate set.

10. An automated method for collaboratively developing a knowledge base with information from a plurality of editors comprising the steps of:
designating a plurality of editors;
providing to at least one of the plurality of editors a knowledge base activity information comprising an unfulfilled predicate argument information associated with an unfulfilled predicate argument;
inviting an editor input from the at least one of the plurality of editors regarding said unfulfilled predicate argument information;
fulfilling said unfulfilled predicate argument information based upon said editor input to generate a complete predicate set; and
storing said complete predicate set in said knowledge base.

11. The method of claim 10, wherein the step of providing to at least one of the plurality of editors knowledge base activity information comprises the step of posting said knowledge base activity information on an electronic bulletin board accessible to at least one of the plurality of editors.

12. The method of claim 10, wherein the step of inviting editor input comprises the step of providing a natural language query relating to said unfulfilled predicate argument.

13. The method of claim 10, wherein the plurality of editors each have a designated authority level determining a permission level for providing said editor input regarding said unfulfilled predicate argument information.

14. The method of claim 10, further comprising the steps of:
receiving an input predicate argument from at least one of the plurality of editors;
pairing said input predicate argument with said predicate head to generate a complete predicate set; and
storing said complete predicate set in said knowledge base.

15. The method of claim 10, further comprising the steps of:
receiving an input predicate argument from at least one of the plurality of editors; and
storing said input predicate argument as exemplary language features associated with said unfulfilled predicate argument.

* * * * *